United States Patent
Erhart

(10) Patent No.: US 10,992,013 B2
(45) Date of Patent: Apr. 27, 2021

(54) BATTERY SYSTEM FOR A VEHICLE AND METHOD FOR DETECTING AN OVERHEAT SITUATION OF THE BATTERY SYSTEM

(71) Applicant: Samsung SDI Co., Ltd., Yongin-si (KR)

(72) Inventor: Michael Erhart, Pirka-Seiersberg (AT)

(73) Assignee: SAMSUNG SDI CO., LTD., Yongin-si (KR)

(*) Notice: Subject to any disclaimer, the term of this patent is extended or adjusted under 35 U.S.C. 154(b) by 59 days.

(21) Appl. No.: 16/589,509

(22) Filed: Oct. 1, 2019

(65) Prior Publication Data
US 2020/0112016 A1   Apr. 9, 2020

(30) Foreign Application Priority Data

Oct. 5, 2018 (EP) .................................. 18198757
Sep. 17, 2019 (KR) ...................... 10-2019-0114258

(51) Int. Cl.
| | | |
|---|---|---|
| H01M 4/02 | (2006.01) | |
| H01M 50/581 | (2021.01) | |
| G01N 31/22 | (2006.01) | |
| B60L 58/10 | (2019.01) | |
| H01M 10/44 | (2006.01) | |
| H01M 10/48 | (2006.01) | |
| H01M 50/20 | (2021.01) | |
| H01M 50/124 | (2021.01) | |
| H01M 10/0525 | (2010.01) | |

(52) U.S. Cl.
CPC ........... *H01M 50/581* (2021.01); *B60L 58/10* (2019.02); *G01N 31/223* (2013.01); *H01M 10/441* (2013.01); *H01M 10/48* (2013.01); *H01M 50/124* (2021.01); *H01M 50/1245* (2021.01); *H01M 50/20* (2021.01); *H01M 10/0525* (2013.01); *H01M 2200/10* (2013.01); *H01M 2220/20* (2013.01)

(58) Field of Classification Search
CPC ....................................................... H01M 4/02
See application file for complete search history.

(56) References Cited

U.S. PATENT DOCUMENTS

| | | | |
|---|---|---|---|
| 2017/0279168 A1 | 9/2017 | Kato et al. | |
| 2017/0365840 A1* | 12/2017 | Fan | ........................ H01M 2/348 |
| 2018/0003685 A1 | 1/2018 | Cummings et al. | |

FOREIGN PATENT DOCUMENTS

| | | |
|---|---|---|
| DE | 10 2012 215 883 A1 | 3/2014 |
| WO | WO 2016/086184 A1 | 6/2016 |

OTHER PUBLICATIONS

Extended European Search Report issued in European Application No. 18198757.9, dated Apr. 4, 2019, 5 pages.

* cited by examiner

*Primary Examiner* — Jacob B Marks
(74) *Attorney, Agent, or Firm* — Lewis Roca Rothgerber Christie LLP

(57) ABSTRACT

A battery system for a vehicle includes: a battery module including a plurality of secondary battery cells; a gas sensor; and a housing accommodating the battery module and the gas sensor. At least a portion of an exterior surface of the battery module and/or at least a portion of an interior surface of the housing is covered by a coating. The coating is configured to emit a gaseous species when a temperature exceeds a reference temperature, and the gas sensor is configured to detect the gaseous species.

11 Claims, 5 Drawing Sheets

BATTERY SYSTEM FOR A VEHICLE AND METHOD FOR DETECTING AN OVERHEAT SITUATION OF THE BATTERY SYSTEM

CROSS-REFERENCE TO RELATED APPLICATION

This application claims priority to and the benefit of European Patent Application No. 18198757.9, filed in the European Patent Office on Oct. 5, 2018, and Korean Patent Application No. 10-2019-0114258, filed in the Korean Intellectual Property Office on Sep. 17, 2019, the entire content of both of which is incorporated herein by reference.

BACKGROUND

1. Field

Aspects of embodiments of the present invention relate to a battery system for a vehicle and a method for detecting an overheat situation of the battery system.

2. Related Art

In recent years, vehicles for transportation of goods and people have been developed that use electric power as a source for motion. Such electric vehicles are automobiles that are propelled by an electric motor using energy stored in rechargeable batteries. An electric vehicle may be powered solely by batteries or may be a form of hybrid vehicle powered by, for example, a gasoline generator. Furthermore, the vehicle may include a combination of an electric motor and a conventional combustion engine.

Generally, an electric-vehicle battery (EVB) or traction battery is a battery used to power the propulsion of battery electric vehicles (BEVs). Electric-vehicle batteries differ from starting, lighting, and ignition batteries because they are designed to provide power over sustained periods of time.

A rechargeable (or secondary) battery differs from a primary battery in that it is designed to be repeatedly charged and discharged, while the latter provides an irreversible conversion of chemical to electrical energy. Low-capacity rechargeable batteries are used as power supplies for small electronic devices, such as cellular phones, notebook computers, and camcorders, while high-capacity rechargeable batteries are used as power supplies for hybrid vehicles and the like.

Generally, rechargeable batteries include an electrode assembly including a positive electrode, a negative electrode, and a separator interposed between the positive and negative electrodes, a case receiving (or accommodating) the electrode assembly, and an electrode terminal electrically connected to the electrode assembly. An electrolyte solution is injected into the case to enable charging and discharging of the battery via an electrochemical reaction between the positive electrode, the negative electrode, and the electrolyte solution. The shape of the case, for example, cylindrical or rectangular, may be chosen based on the battery's intended purpose. Lithium-ion (and similar lithium polymer) batteries, widely known via their use in laptops and consumer electronics, dominate the most recent electric vehicles in development.

Rechargeable batteries may be used as a battery module formed of a plurality of unit battery cells coupled to each other in series and/or in parallel to provide high energy density for, as an example, driving a motor of a hybrid vehicle. For example, the battery module may be formed by interconnecting the electrode terminals of the plurality of unit battery cells, the number of the unit battery cells depending on a desired amount of power, in order to realize a high-power rechargeable battery.

A battery pack may include any suitable number of (preferably identical) battery modules. The battery modules may be configured in (e.g., connected to each other in) series, parallel, or a mixture of both to provide the desired voltage, capacity, and/or power density. Components of the battery packs include the individual battery modules and interconnections, which provide electrical conductivity between the battery modules.

Static control of battery power output and charging may not be sufficient to meet the dynamic power demands of various electrical consumers connected to the battery system. Thus, steady exchange of information between the battery system and the controllers of the electrical consumers may be provided. This information includes the battery systems actual state of charge (SoC), potential electrical performance, charging ability, and internal resistance as well as actual or predicted power demands or surpluses of the consumers.

Battery systems generally include a battery management system (BMS) and/or a battery management unit (BMU) for processing the aforementioned information. The BMS/BMU may communicate with the controllers of the various electrical consumers via a suitable communication bus, such as a SPI or CAN interface. The BMS/BMU may further communicate with each of the battery submodules, for example, with a cell supervision circuit (CSC) of each battery submodule. The CSC may be connected to a cell connection and sensing unit (CCU) of a battery submodule that interconnects the battery cells of the battery submodule.

Thus, the BMS/BMU may be provided to manage the battery pack, such as by protecting the battery from operating outside its safe operating area, monitoring its state, calculating secondary data, reporting that data, controlling its environment, authenticating it, and/or balancing it.

To provide thermal control of the battery pack, a thermal management system may be provided to safely use the at least one battery module by efficiently emitting, discharging, and/or dissipating heat generated from its rechargeable batteries. If the heat emission/discharge/dissipation is not sufficiently performed, temperature deviations occur between respective battery cells, such that the at least one battery module may not generate a desired amount of power. In addition, an increase of the internal temperature may lead to abnormal reactions occurring therein, and thus, charging and discharging performance of the rechargeable deteriorates and the life-span of the rechargeable battery is shortened. Thus, cell cooling for effectively emitting/discharging/dissipating heat from the cells is desired.

Safety requirements, including the protection of passengers of a vehicle from harmful effluents of the battery system, such as toxic gases, smoke, or the like, are usually provided by a gas tight housing enclosing the battery modules and BMS/BMU to restrict or prevent the emission of such effluents.

However, while the system housing may protect the passengers from harmful fumes, it complicates detection of critical states of the battery system that may lead to a catastrophic event, such as an explosion of the battery system. Such catastrophic events may be caused by an overheat situation. Generally, the BMS/BMU can detect an overheat situation based only on acquired measurements regarding voltage, current, and temperature, as some examples. Hence, abnormal states which do not change (or affect) the voltage, current, temperature, or electrical insulation value are not yet detectable. However, not all failures can be detected in a reasonable time. For example, badly screwed busbars may produce high power dissipation and heat, which can overheat cells or other internal elements, which may end in destruction of cells or relays. Due to limited installation space and cost saving reasons, not all cells and busbar interconnections are supervised by temperature sensors.

It is thus an object of embodiments of the present invention to overcome or mitigate at least some of the drawbacks of the prior art and to provide a battery system that allows for improved detection of an overheat situation of the battery system, particularly of such abnormal states that do not (or do not substantially) alter the voltage, current, or temperature of the total battery system.

SUMMARY

Aspects of embodiments of the present invention seek to solve or mitigate at least one of the problems existing in the prior art. In one embodiment, a battery system for a vehicle includes: a battery module including a plurality of secondary battery cells; a gas sensor; and a housing accommodating the battery module and the gas sensor.

According to embodiments of the present invention, at least portions of an exterior surface of the battery modules and/or at least portions of an interior surface of the housing are covered by a coating that is configured to emit a gaseous species when a temperature exceeds a reference temperature. The gas sensor is configured to detect the gaseous species.

According to embodiments of the present invention, a thermally sensitive coating is deposited on surfaces of the battery system. When the temperature of the coating reaches a reference threshold, the coating starts to emit a gaseous species. Said gaseous species is then detected by the gas sensor, which is provided in the interior space of the battery system. A battery management system (BMS) may be in direct communication with the gas sensor and, for example, may initiate safety and emergency measures, if necessary. In other words, a simple but robust temperature control may be established within the housing encompassing the battery module(s) of the battery system. Thereby, overheating may be detected in areas of the battery system not accessible by conventional temperature sensors.

The coating may include (or may be formed of or may consist of) at least one of: (i) a reactive system that produces the gaseous species by a chemical reaction at the reference temperature; (ii) a compound having a boiling point or a sublimation point at the reference temperature, wherein the gaseous phase of the compound represents the gaseous species; and (iii) a matrix system that includes the gaseous species and is configured to emit the gaseous species at the reference temperature.

According to option (i), the coating includes (or consists of) one or more components which convert into the gaseous species when the temperature reaches the reference temperature. For example, a compound may start to decompose into the gaseous species at a certain temperature or a chemical reaction between two compounds resulting in the creation of the gaseous species will be thermally initiated when a certain temperature is reached.

According to option (ii), the coating includes a liquid or solid compound, which is transferred into its gaseous phase when the temperature reaches the boiling or sublimation point of the compound.

According to option (iii), a matrix system will set the gaseous species free when the temperature reaches a certain temperature. For example, the gaseous species may be fixed in stable foam, which decomposes when the temperature exceeds a certain temperature.

The gas sensor is sensitive to (e.g., is configured to detect) the gaseous species. In other words, gaseous species and gas sensor should be compatible.

The reference (or predetermined) temperature is based on the material of the coating. Thus, one skilled in the art may select the specific composition of the coating with respect to desired operating parameters or requirements of the battery system. For example, if the temperature at a certain surface of the battery module or housing should not exceed about 80° C., a coating which will emit a detectable amount of the gaseous species when it reaches a temperature of about 80 C may be deposited. For example, a compound for the coating having a boiling point or a sublimation point at around 80° C., such like cyclohexane, may be used.

A suitable reference temperature may vary significantly for each battery system. Moreover, within a certain battery system, different coatings sensitive to different temperatures may be reasonable. For example, some embodiments of the present invention include coatings having different reference (e.g., boiling or sublimation) temperatures covering a relatively broad temperature range. However, a useful coating composition for a certain temperature may be simply identified by using a chemical database, like chemical abstracts, listening boiling points of compounds.

In some embodiments, the coating is provided on at least one of: an exterior surface of a battery cell; an electrical wiring of the battery system; and a cooling element for battery cells and battery modules.

For example, the coating may be deposited on portions the battery cell case or a cap plate covering an opening in the case. Thereby, supervision of overheating of each battery cell may be easily established. In other words, battery cells, busbars, screws etc. of the battery module may be coated. In the case of an overheat situation of these components, the coating will degas characteristic compounds, which will be detected by the gas sensor configured to detect the characteristic compound(s).

The electrical wiring of the battery system includes the interconnection of battery cell terminals within a battery module, the interconnection of the battery modules, and the system terminals of the battery system. For example, the electric wiring may include high or low current connectors, and the coating is disposed on these current connectors. Thus, even a single current connector overheating may be easily detected.

The coating may also be provided at a cooling element, like cooling plates. Hence, a failure of a cooling element may be detected prior to any harmful rise of temperature in the battery cells.

As mentioned above, the battery system may include different coatings at different places. For example, the coating of low current connectors may be different from the coating applied to high current connectors, and the coatings may emit different gas species at different temperatures. According to another embodiment, a single coating may emit different gaseous species at different temperatures in order to distinguish different overheat situations according to the overheat temperature.

According to one embodiment, the battery system further includes a means for forming a circulating air stream within the housing, the air stream flowing over the surfaces at where the coating is applied with the gas sensor being placed within the air stream. For example, the means for forming the air stream may include a fan, and the gas sensor may be placed within the air stream leaving the fan. By establishing a suitable air stream loop within the housing, the gaseous species will be transferred to the gas sensor, and thus, it is not necessary to place the gas sensor next to the coating. Moreover, a single gas sensor may be used to control (e.g., to sense) the emission of several coatings because, for security reasons, it is mostly sufficient to know that a thermal fault occurred somewhere in the battery system.

According to another embodiment, which may be combined with any of the before or later mentioned embodiments, the battery system further includes a battery management system (BMS) connected to the gas sensor, and the gas sensor is configured to transmit a control signal to the BMS in response to detecting the gaseous species. The battery system may further include a battery disconnect unit (BDU) interconnected between at least one of a first and second system terminal and the battery module. The BMS may be configured to transmit a disconnect signal DS to the BDU in response to receiving the control signal CS, and the BDU may be configured to disconnect at least one of the first and second system terminal and the battery module in response to the disconnect signal DS. Thus, the detection of a certain gaseous species will immediately initiate safety measurements within the BMS itself.

According to another embodiment of the present invention, a vehicle including the battery system is provided.

According to another embodiment of the present invention, a method for detecting an overheat situation of a battery system is provided. The battery system includes: a battery management system (BMS); a battery module including a plurality of secondary battery cells; a gas sensor; and a housing accommodating the battery module and the gas sensor, wherein at least a portion of the exterior surface of the battery module and/or at least a portion of the interior surface of the housing is covered by a coating that is configured to emit a gaseous species when a temperature exceeds a reference temperature, and wherein the gas sensor is configured to detect the gaseous species. The method includes: b) detecting the gas species with the gas sensor; and transmitting a control signal CS from the gas sensor to the BMS in response to the detection of the gas species. The method may further include: determining an overheat situation in the battery system; and controlling a countermeasure to the overheat situation.

Aspects of embodiments of the present invention also relate to a method for detecting an overheat situation of a battery system including a battery module interconnected between a first system terminal and a second system terminal by a plurality of high current connectors and including a housing with a plurality of exterior walls enclosing the battery module and the plurality of high current connectors. The method includes providing a coating that is configured to emit the gaseous species at a temperature higher than a reference temperature threshold on least portions of the battery module and/or the plurality of high current connectors; detecting a concentration of the gaseous species in the housing; and transmitting the control signal CS in response to the detection of an excess concentration of the gaseous species.

Various methods, according to embodiments of the present invention, may be employed in battery systems employed for different purposes, such as in battery systems employed in vehicles. Independent of the actual application of the battery system, the transmission of the control signal may severely intervene with the normal operation of the battery system. Hence, false positive events that erroneously indicate an abnormal condition of the battery system should be prevented. On the other hand, early signs of imminent failures of components within the battery system should not be ignored, and the battery system should be brought to a safe state as early as possible in order to reliably prevent catastrophic events, for example, a battery fire. Methods, according to embodiments of the present invention, provide such a reliable solution for detecting early signs of an overheat situation of a battery system as well as for estimating the state of health of safety critical components the battery system.

According to methods of embodiments of the present invention, the state of the battery system is determined based on the concentration of the gaseous species in the battery system. For example, a control signal is transmitted if the concentration of the gaseous species exceeds a reference (or predetermined or learned) threshold for that concentration. For example, a specific control signal from among a plurality of control signals is transmitted in response to the detection an excess (e.g., a predetermined or learned excess) concentration of one or more gaseous species. In some embodiments, a specific control signal from among a plurality of control signals is transmitted in response to the detection a combination of excess concentrations for a plurality of gaseous species. The combination of excess concentrations that may occur in the battery system for an overheat situation may depend on the coatings of the specific portions that are overheating or of the specific temperature value of the overheat situation.

In the following Table 1, a plurality of gaseous species that may be emitted during different overheat situations in a conventional battery system are shown. The gaseous species emitted by the coating(s) according to embodiments of the present invention differ from the below-described gaseous species in type and/or in magnitude of concentration in order to simplify the detection of an overheat situation and to avoid crosstalk.

TABLE 1

| | hot spots, plastic smoldering | electric arc between live components | cell venting (thermal runaway) | fire |
|---|---|---|---|---|
| carbon dioxide ($CO_2$) | x | | x | x |
| carbon monoxide (CO) | x | | x | x |
| hydrogen ($H_2$) | | | x | |
| oxygen ($O_2$) | | | | |
| nitrogen oxides ($NO_x$) | | x | | |
| ozone ($O_3$) | | x | | |
| water vapor ($H_2O$) | x | | | |
| Hydro-carbons | | | x | x |
| smoke/particles | x | x | x | x |

For example, in response to receiving the control signal(s) and/or the determination of an abnormal condition in the battery system, at least one of the first system terminal and the second terminal is disconnected from the battery module, the battery system is switched to an emergency mode, a notification is transmitted to a user of the battery system, cooling of the battery system is increased, a power state (SOP) of the battery system is reduced, and/or a fire extinguishing system for the battery system is triggered.

The controlling or controlling to perform a countermeasure may include transmitting a countermeasure control signal to an entity (e.g., a device or component) that shall actually perform the countermeasure. For example, the controlling or controlling to perform a countermeasure may include transmitting a countermeasure control signal via a battery management system (BMS) interface to an exterior of the battery system. The controlling or controlling to perform a countermeasure may include transmitting, via the BMS interface, a disconnect signal as countermeasure control signal to a battery disconnect unit (BDU) to control the BDU to disconnect at least one of the first and second system terminals from the battery module.

Further aspects and features of embodiments of the present invention may be learned from the dependent claims and/or the following description.

BRIEF DESCRIPTION OF THE DRAWINGS

Aspects and features of the present invention will become apparent to those of ordinary skill in the art by describing, in detail, exemplary embodiments thereof with reference to the attached drawing in which.

DETAILED DESCRIPTION

Figure 1:
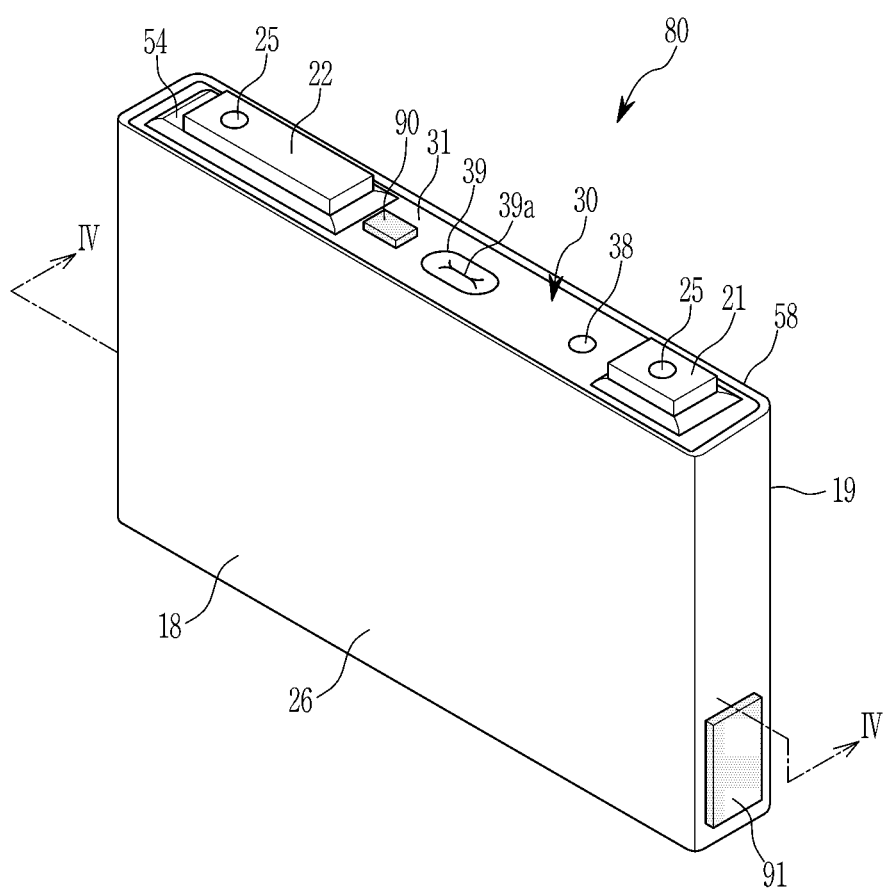
FIG. 1 is a schematic perspective view of a battery cell according to an embodiment of the present invention.

Reference will now be made, in detail, to embodiments, examples of which are illustrated in the accompanying drawings. Aspects and features of the exemplary embodiments, and implementation methods thereof, will be described with reference to the accompanying drawings. In the drawings, like reference numerals denote like elements, and redundant descriptions may be omitted. As used herein, the term "and/or" includes any and all combinations of one or more of the associated listed items. Further, the use of "may" when describing embodiments of the present invention refers to "one or more embodiments of the present invention."

Unless otherwise defined, all terms (including technical and scientific terms) used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and/or the present specification and should not be interpreted in an idealized or overly formal sense, unless expressly so defined herein.

It will be understood that when an element or layer is referred to as being "on," "connected to," or "coupled to" another element or layer, it may be directly on, connected, or coupled to the other element or layer or one or more intervening elements or layers may also be present. When an element or layer is referred to as being "directly on," "directly connected to," or "directly coupled to" another element or layer, there are no intervening elements or layers present. For example, when a first element is described as being "coupled" or "connected" to a second element, the first element may be directly coupled or connected to the second element or the first element may be indirectly coupled or connected to the second element via one or more intervening elements.

The same reference numerals designate the same elements. Expressions, such as "at least one of," when preceding a list of elements, modify the entire list of elements and do not modify the individual elements of the list. Also, the term "exemplary" is intended to refer to an example or illustration. As used herein, the terms "use," "using," and "used" may be considered synonymous with the terms "utilize," "utilizing," and "utilized," respectively. As used herein, the terms "substantially," "about," and similar terms are used as terms of approximation and not as terms of degree, and are intended to account for the inherent variations in measured or calculated values that would be recognized by those of ordinary skill in the art.

It will be understood that, although the terms first, second, third, etc. may be used herein to describe various elements, components, regions, layers, and/or sections, these elements, components, regions, layers, and/or sections should not be limited by these terms. These terms are used to distinguish one element, component, region, layer, or section from another element, component, region, layer, or section. Thus, a first element, component, region, layer, or section discussed below could be termed a second element, component, region, layer, or section without departing from the teachings of example embodiments. In the figures, dimensions of the various elements, layers, etc. may be exaggerated for clarity of illustration.

Spatially relative terms, such as "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" or "over" the other elements or features. Thus, the term "below" may encompass both an orientation of above and below. The device may be otherwise oriented (rotated 90 degrees or at other orientations), and the spatially relative descriptors used herein should be interpreted accordingly.

The terminology used herein is for the purpose of describing particular example embodiments of the present invention and is not intended to be limiting of the described example embodiments of the present invention. As used herein, the singular forms "a" and "an" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components but do not preclude the presence or addition of one or more other features, integers, steps, operations, elements, components, and/or groups thereof.

Figure 2:
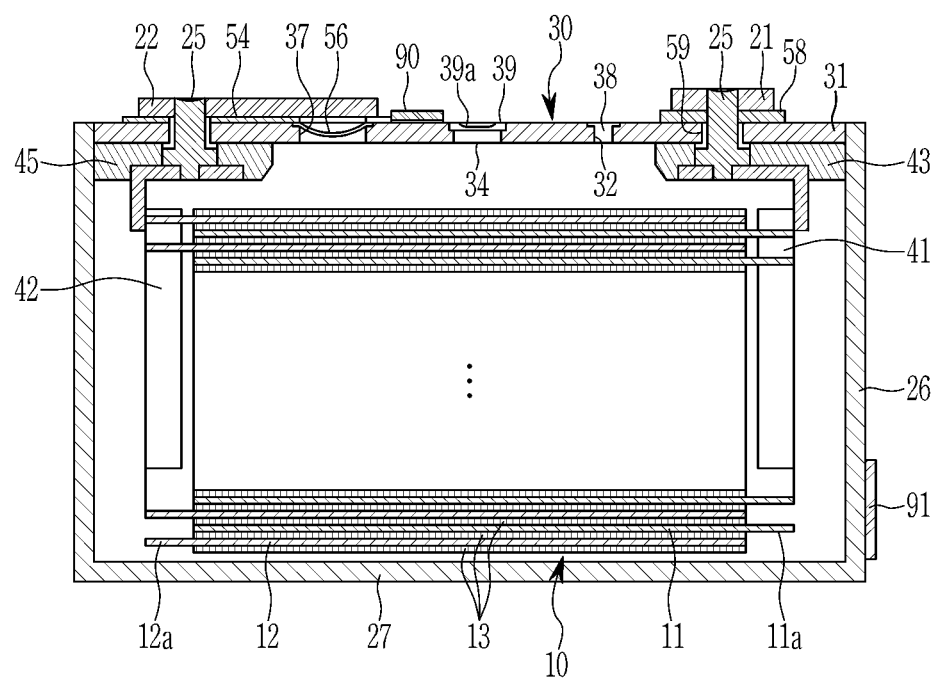
FIG. 2 is a schematic cross section of the battery cell shown in FIG. 1.

FIG. 1 is a perspective view illustrating a battery cell according to an exemplary embodiment, and FIG. 2 is a cross-sectional view taken along the line IV-IV of FIG. 1.

As shown in FIGS. 1 and 2, the battery cell 80 according to an embodiment may include an electrode assembly 10, and a case 26 accommodating the electrode assembly 10. The case 26 may contain an electrolyte. The battery cell 80 may further include a cap assembly 30 for sealing an opening in the case 26. The battery cell 80 will be described as a lithium ion secondary battery having a prismatic shape as a non-limiting example.

The electrode assembly 10 may be formed as a jelly roll type electrode assembly by spirally winding a positive electrode 11 and a negative electrode 12 with a separator 13 therebetween. The positive electrode 11 and the negative electrode 12 may respectively include current collectors formed of a thin metal foil having coated regions on which an active material may be coated and may respectively include positive and negative electrode uncoated regions 11a and 12a of the current collectors on which no active material is coated. As a non-limiting example, the coated region of the positive electrode 11 may be formed by coating a base material formed of a metal foil, such as an aluminum foil, with an active material, such as transition metal oxide or the like. The coated region of the negative electrode 12 may be formed by coating a base material formed of a metal foil, such as a copper or nickel foil, with an active material, such as carbon, graphite, or the like.

The positive electrode uncoated region 11a may be formed on one lateral end of the positive electrode 11 in a longitudinal direction of the positive electrode 11, and the negative electrode uncoated region 12a may be formed on one lateral end of the negative electrode 12 in a longitudinal direction of the negative electrode 12. The positive electrode uncoated region 11a and the negative electrode uncoated region 12a may be on opposite sides with respect to the coated regions. Further, the separator 13 may include a plurality of separators 13, which may be spirally wound after the positive electrode 11, the negative electrode 12, and the separator(s) 13 are alternately situated. The present invention is not limited thereto, however, and the electrode assembly 10 may be configured to have a structure including a plurality of sheets of the positive electrode 11, the separator 13, and the negative electrode 12 that are repeatedly stacked.

The electrode assembly 10 may be accommodated in the case 26 together with an electrolyte solution. The electrolyte solution may be made of (or may include) a lithium salt, such as $LiPF_6$ or $LiBF_4$, with an organic solvent, such as EC, PC, DEC, EMC, or EMC. The electrolyte solution may be in a liquid, solid, or gel state. The case 26 may have a substantially cuboidal shape, and an opening may be formed at one side thereof. The case 26 may be formed of a metal, such as aluminum.

The case 26 may have a bottom surface 27 having a substantially rectangular shape and may include a pair of first lateral walls that are wide side surfaces 18, 19 and a pair of second lateral walls that are narrow side surfaces, connected vertically to end portions of the bottom surface 27, respectively, to form a space for accommodating the electrode assembly 10. The first lateral walls 18, 19 may face each other, and the second lateral walls may face each other and may be connected to the first lateral walls 18, 19. A length of an edge at which the bottom surface 27 and a first lateral wall 18, 19 are connected to each other may be longer than an edge at which the bottom surface 27 and the second lateral wall are connected to each other. In some embodiments, adjacent first and second lateral walls enclose (or form) an angle of about 90°.

The cap assembly 30 may include a cap plate 31 for covering (or sealing) the opening in the case 26 by being bonded to the case 26, and the cap assembly 30 may include a positive terminal (e.g., a first terminal) 21 and a negative terminal (e.g., second terminal) 22, which externally protrude from the cap plate 31 and are electrically connected to the positive electrode 11 and the negative electrode 12, respectively. The cap plate 31 may be configured to have a plate shape that may extend in one direction, and the cap plate 31 may be bonded to the opening in the case 26. The cap plate 31 may include an injection opening (e.g., an injection hole) 32 and a vent opening (e.g., a vent hole) 34 that communicate with (e.g., open to) an interior of the case 26. The injection opening 32 may be configured to allow the injection of the electrolyte solution, and a sealing cap 38 may be mounted thereon or therein. Further, a vent member 39 including a notch 39a, which may open due to a reference pressure (e.g., a predetermined pressure) in the case 26 may be mounted to or in the vent opening 34.

The positive terminal 21 and the negative terminal 22 may be mounted to protrude upwardly from the cap plate 31. The positive terminal 21 may be electrically connected to the positive electrode 11 via a current collecting tab 41, and the negative terminal 22 may be electrically connected to the negative electrode 12 via a current collecting tab 42. A terminal connecting member 25 for electrically connecting the positive terminal 21 and the current collecting tab 41 to each other may be mounted between the positive terminal 21 and the current collecting tab 41. The terminal connecting member 25 may be inserted into an opening (e.g., a hole) formed in the positive terminal 21 such that a lower portion of the terminal connecting member 25 may be welded to the current collecting tab 41.

A gasket 59 may be mounted between the terminal connecting member 25 and the cap plate 31 while being inserted into the opening in the cap plate 31 through which the terminal connecting member 25 extends to seal therebetween. Further, a lower insulating member 43, into which the lower portion of the terminal connecting member 25 may be inserted, may be mounted under the cap plate 31. A connecting plate 58 for electrically connecting the positive terminal 21 and the cap plate 31 may be mounted between the positive terminal 21 and the cap plate 31. The terminal connecting member 25 may be inserted into (e.g., may extend through) the connecting plate 58. Accordingly, the cap plate 31 and the case 26 may be positively electrified.

A terminal connecting member 25 for electrically connecting the negative terminal 22 and the current collecting tab 42 to each other, which is similar to the terminal connecting member 25 described above, may be installed between the negative terminal 22 and the current collecting tab 42. The terminal connecting member 25 may be inserted into an opening (e.g., a hole) formed in the negative terminal 22 such that an upper portion and a lower portion of the terminal connecting member 25 may be welded to the negative terminal 22 and to the current collecting tab 42, respectively. A gasket, which is similar to the gasket 59 described above, may be mounted between the negative terminal 22 and the cap plate 31 while being inserted into an opening (e.g., a hole) through which the terminal connecting member 25 may extend to seal therebetween. Further, a lower insulating member 45, which is for insulating the negative terminal 22 and the current collecting tab 42 from the cap plate 31, may be mounted under the cap plate 31.

An upper insulating member 54 for electrically insulating the negative terminal 22 and the cap plate 31 may be mounted between the negative terminal 22 and the cap plate 31. The terminal connecting member 25 may be inserted into (e.g., may pass or extend through) an opening (e.g., a hole) formed in the upper insulating member 54. The cap assembly 30 may include a short-circuiting opening (e.g., a short-circuit opening or hole) 37, and a short-circuiting member (e.g., a short-circuit member) 56 that may (e.g., may selectively or may be configured to) short-circuit the positive electrode 11 and the negative electrode 12 through (e.g., installed in) the short-circuiting opening 37. The short-circuiting member 56 may be between the upper insulating member 54 and the cap plate 31, and the upper insulating member 54 may have a cutout (e.g., an opening) formed at a position corresponding to the short-circuiting member 56. The short-circuiting member 56 may overlap the negative terminal 22 exposed through the cutout and may be separately located (e.g., may be spaced from the negative terminal 22).

Further, the short-circuiting member 56 may be between the negative terminal 22 and the vent opening 34 and may be located closer to the negative terminal 22 than to the vent opening 34. The short-circuiting member 56 may include a convexly curved portion that (e.g., that in a normal configuration) curves toward the electrode assembly 10 and may include an edge portion may be formed at an outside of the curved portion and that is fixed to the cap plate 31. The short-circuiting member 56 may be deformed (e.g., may be configured to deform) to cause a short-circuit when an internal pressure of the battery cell 80 rises (e.g., rises above a reference pressure). For example, the internal pressure of the battery cell 80 may rise when gas is generated by an unwanted reaction in the battery cell 80. When the internal pressure of the battery cell 80 is increased above a reference level (e.g., a predetermined level), the curved portion may deform to be concavely curved toward an opposite direction, thereby causing the short-circuiting member 56 to contact the negative terminal 22 to cause a short-circuit.

According to the exemplary embodiment illustrated in FIGS. 1 and 2, a first coating 90 is disposed on a part of the cap plate 31 and a second coating 91 is disposed on a part of a side surface of the case 26. However, the arrangement of the first and second coatings 90, 91 is not limited thereto. The coatings may be deposited on any surface of the battery cell 80 which will be accessible to (e.g., exposed to) air within a housing of the battery system as will be explained in more detail below. The coatings 90, 91 are configured to emit at least one gaseous species when a temperature (e.g., a temperature of the case 26 or of the surrounding environment) exceeds a reference temperature (e.g., a predetermined temperature). In some embodiments, the first and second coatings 90, 91 have the same composition, i.e., will emit the same gaseous species when the temperature exceeds the same reference temperature. However, in some embodiments, the first and second coatings 90, 91 may have different compositions configured to emit different gaseous species at, for example, different reference temperatures. The coatings 90, 91 may include (or may be formed or may consist of) at least one of: (i) a reactive system that produces the at least one gaseous species by a chemical reaction at the reference temperature; (ii) a compound having a boiling point or a sublimation point at the reference temperature, wherein the gaseous phase of the compound represents the gaseous species; and (iii) a matrix system that includes the gaseous species and is configured to emit the gaseous species at the reference temperature.

Figure 3:
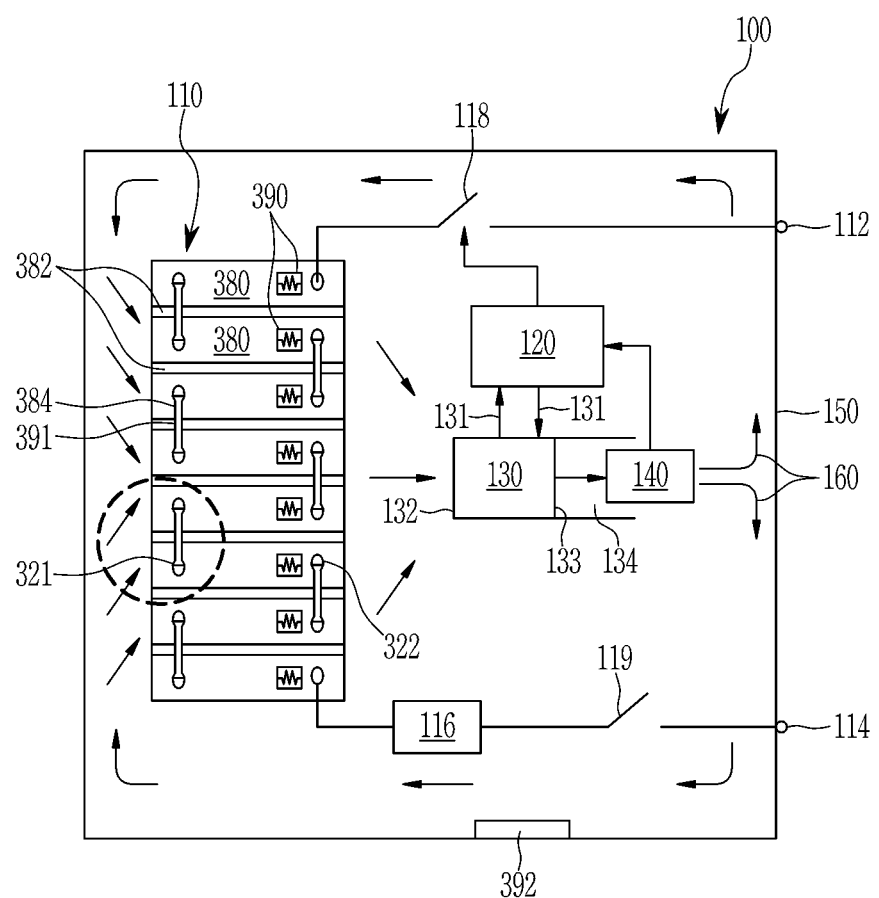
FIG. 3 is a schematic illustration of a battery system according to an embodiment of the present invention.

FIG. 3 schematically illustrates a top view of a battery system 100 according to an embodiment of the present invention. The battery system 100 includes a stack of battery cells 380 being assembled and electrically interconnected to form a battery module 110. The battery cells 380 of the battery module 110 may be similar to the battery cell 80 described above with reference to FIGS. 1 and 2. Cooling plates 382 are disposed between adjacent battery cells 380, and a coating 390, similar to the coating 90 of the embodiment shown in FIG. 1, is disposed on the top surface of each of the battery cells 380.

Figure 4:
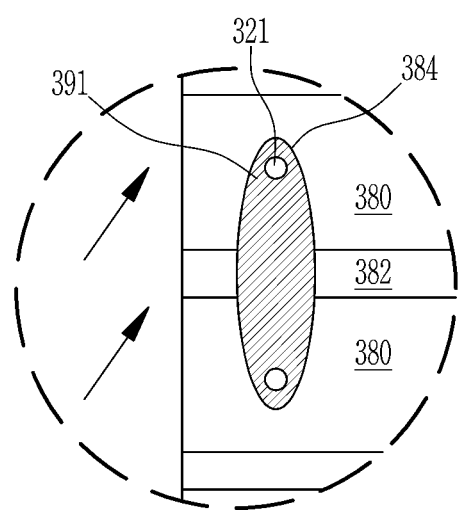
FIG. 4 is an enlarged view of a part of the battery system shown in FIG. 3.

The negative and positive terminals 321, 322 of neighboring battery cells 380 are interconnected by high current connectors 384. As shown in more detail in FIG. 4, a coating 391, which emits at least one gaseous species when a temperature exceeds a reference temperature (e.g., a predetermined temperature), is disposed on the entire upper surface of the high current connectors 384. Thus, the battery module 110 is interconnected between a first system terminal 112 and a second system terminal 114 by the plurality of high current connectors 384. The interconnection may further include a current sensor 116 and relays 118, 119 for connecting and disconnecting, respectively, the system terminals 112, 114 to and from the battery module 110.

The battery system 100 further includes a battery management system (BMS) 120. The BMS 120 may communicate to controllers of the various electrical consumers via a suitable communication bus, such as a SPI or CAN interface. The BMS 120 may further communicate with a cell supervision circuit (CSC) of each battery module 110. Thus, the BMS 120 is provided to manage the battery system 100, such as by protecting the battery cells 380 from operating outside their safe operating area, monitoring their state, calculating secondary data, reporting that data, etc. In some embodiments, the BMS 120 also communicates with a battery disconnect unit (BDU).

In the embodiment of the present invention illustrated in FIG. 3, the battery system 100 further includes a fan 130. The BMS 120 may regulate and supervise the activity and status of the fan 130 via data lines 131. An inlet opening 132 of the fan 130 is provided on a side of the fan 130 facing the battery module 110. An outlet opening 133 of the fan 130 is positioned opposite to the inlet opening 132 thereof and opens out, into a flow channel 134. A gas sensor 140 is positioned within the flow channel 134.

Furthermore, a housing 150 is provided for accommodating the battery module(s) 110, the BMS 120, the fan 130, and the gas sensor 140. The housing 150 may include a rigid frame structure and cover elements for hermetically closing (and sealing) the battery system 100. The housing 150 may be mounted to the underbody of an electric vehicle. In the illustrated embodiment, a coating 392, which emits at least one gaseous species when a temperature exceeds a reference temperature, is disposed on an interior surface of the housing 150.

When the fan 130 is switched on, a circulating air stream indicated by arrows 160 is formed within the housing 150. The air stream flows over each surface where the coatings 390, 391, 392 are applied, and the gas sensor 140 is placed within said air stream. When the temperature at the coatings 390, 391, 392 exceeds a reference temperature, a gaseous species will be emitted by the corresponding coating(s) 390, 391, 392 and will be transferred by the air flow towards the gas sensor 140. The gas sensor 140 may be selective for (e.g., may selectively detect) the gaseous species.

Figure 5:
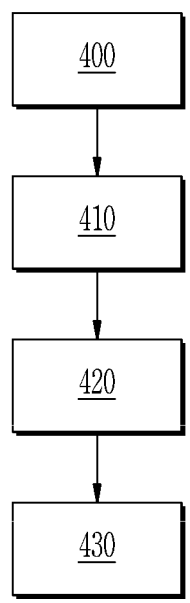
FIG. 5 is a flow chart illustrating a method for detecting an overheat situation of a battery system according to an embodiment of the present invention.

As schematically illustrated in the flow chart of FIG. 5, detection of the gaseous species by the gas sensor 140 causes output of a control signal CS by the gas sensor 140 (Step 400), followed by transmission of the control signal CS to the BMS 120 (Step 410). In response to the control signal CS, the BMS 120 may initiate disconnection between the first and second system terminals 112, 114 by means of the battery disconnect unit (BDU) (Step 420). For example, the BMS 120 is configured to transmit a disconnect signal DS to the BDU in response to receiving the control signal CS, and the BDU is configured to disconnect at least one of the first and second system terminals 112, 114, for example, by switching relay 118 (Step 430). Thus, the BMS 120 determines, based on the control signal CS from the gas sensor 140, the presence of an overheat situation in the battery system 100 and controls at least one countermeasure to said overheat situation, for example, disconnection of the battery module 110.

SOME REFERENCE NUMERALS

10 electrode assembly
11 positive electrode
11a positive electrode uncoated region
12 negative electrode
12a negative electrode uncoated region
13 separator
18 first lateral side surface
19 second lateral side surface
21, 321 positive cell terminal
22, 322 negative cell terminal
25 terminal connecting member
26 case
27 bottom surface
30 cap assembly
31 cap plate
32 injection opening
34 vent opening
37 short-circuiting opening
38 sealing cap
39 vent member
39a notch
41, 42 current collecting tab
43, 45 lower insulating member
54 upper insulating member
56 short-circuiting member
58 connecting plane
59 gasket
80, 380 battery cell
90, 91, 390, 391, 392 coating for emitting gaseous species
100 battery system
110 battery module
112, 114 first and second system terminals
116 current sensor
118, 119 relay
120 battery management system (BMS)
130 fan
132 inlet opening
133 outlet opening
134 flow channel
140 gas sensor
150 housing
160 arrows indication circulating air stream
382 cooling plate
384 high current connector

What is claimed is:

1. A battery system for a vehicle, the battery system comprising:
    a battery module comprising a plurality of secondary battery cells;
    a gas sensor; and
    a housing accommodating the battery module and the gas sensor,
    wherein at least a portion of an exterior surface of the battery module and/or at least a portion of an interior surface of the housing is covered by a coating, the coating being configured to emit a gaseous species when a temperature exceeds a reference temperature, and
    wherein the gas sensor is configured to detect the gaseous species.

2. The battery system of claim 1, wherein the coating comprises at least one of:
    (i) a reactive system that produces the gaseous species by a chemical reaction at the reference temperature;
    (ii) a compound having a boiling point or a sublimation point at the reference temperature, wherein a gaseous phase of the compound represents the gaseous species; and
    (iii) a matrix system comprising the gaseous species and that is configured to emit the gaseous species at the reference temperature.

3. The battery system of claim 1, wherein the coating is on at least one of:
    an exterior surface of a battery cell;
    an electrical wiring of the battery system; and
    a cooling element for battery cells and battery modules.

4. The battery system of claim 3, wherein the electrical wiring comprises current connectors, and
    wherein the coating is on the current connectors.

5. The battery system of claim 1, further comprising a means for forming a circulating air stream within the housing,
    wherein the air stream flows over the surfaces at where the coating is applied, and
    wherein the gas sensor is within the air stream.

6. The battery system of claim 5, wherein the means for forming the air stream comprises a fan, and
    wherein the gas sensor is within the air stream leaving the fan.

7. The battery system of claim 1, further comprising a battery management system (BMS) connected to the gas sensor,
    wherein the gas sensor is configured to transmit a control signal to the BMS in response to detecting the gaseous species.

8. The battery system of claim 7, further comprising a battery disconnect unit (BDU) interconnected between at least one of a first and second system terminals of the battery system and the battery module,
    wherein the BMS is configured to transmit a disconnect signal to the BDU in response to receiving the control signal, and
    wherein the BDU is configured to disconnect at least one of the first and second system terminals from the battery module in response to the disconnect signal.

9. A vehicle comprising the battery system of claim 1.

10. A method for detecting an overheat situation of a battery system, the battery system comprising: a battery module comprising a plurality of secondary battery cells; a gas sensor; a housing accommodating the battery module and the gas sensor; and a battery management system (BMS), wherein at least a portion of an exterior surface of the battery module and/or at least a portion of an interior surface of the housing is covered by a coating, the coating being configured to emit a gaseous species when a temperature exceeds a reference temperature, and wherein the gas sensor is configured to detect the gaseous species, the method comprising:
    detecting the gas species with the gas sensor; and
    transmitting a control signal from the gas sensor to the BMS in response to the detection of the gas species.

11. The method of claim 10, further comprising:
determining an overheat situation in the battery system; and
controlling a countermeasure to the overheat situation.

* * * * *